(12) United States Patent
Hirata et al.

(10) Patent No.: US 7,928,253 B2
(45) Date of Patent: Apr. 19, 2011

(54) METHOD OF PRODUCING 6,6-DIMETHYL-3-OXABICYCLO[3.1.0]HEXAN-2-ONE

(75) Inventors: Norihiko Hirata, Osaka (JP); Toshitsugi Uemura, Osaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 531 days.

(21) Appl. No.: 12/091,200

(22) PCT Filed: Jun. 28, 2006

(86) PCT No.: PCT/JP2006/313357
§ 371 (c)(1),
(2), (4) Date: May 21, 2008

(87) PCT Pub. No.: WO2007/052383
PCT Pub. Date: May 10, 2007

(65) Prior Publication Data
US 2010/0168463 A1 Jul. 1, 2010

(30) Foreign Application Priority Data

Nov. 1, 2005 (JP) ................................. 2005-318071
Apr. 17, 2006 (JP) ................................. 2006-113071

(51) Int. Cl.
*C07D 307/93* (2006.01)
(52) U.S. Cl. .................................................... 549/462
(58) Field of Classification Search ................ 549/462
See application file for complete search history.

(56) References Cited

FOREIGN PATENT DOCUMENTS

| EP | 0031041 A2 | 7/1981 |
|----|------------|--------|
| EP | 0101991 A1 | 3/1984 |
| EP | 1120401 A2 | 8/2001 |
| EP | 1120402 A2 | 8/2001 |
| EP | 1683782 A2 | 7/2006 |
| EP | 1683783 A2 | 7/2006 |
| JP | 56-87533 A | 7/1981 |
| JP | 58-103379 A | 6/1983 |
| JP | 6-145163 A | 5/1994 |
| JP | 2001-278853 A | 10/2001 |
| JP | 2004-51499 A | 2/2004 |

OTHER PUBLICATIONS

T. Kajiwara et al., "Synthesis and thermal isomerization of dictyopterene A and related compounds", Bulletin of the institute for chemical research, Kyoto University, (1971), vol. 49, No. 3, pp. 179-199.

Michael P. Doyle and Roland J. Pieters, "High Enantioselectivity in the Intramolecular Cyclopropanation of Allyl Diazoacetates Using a Novel Rhodium(II) Catalyst", J. Am. Chem. Soc., vol. 113, 1991, pp. 1423-1424.

Hisao Nishiyama et al., "Chiral Ruthenium(II)-Bis(2-oxazolin-2-yl)pyridine Complexes. Asymmetric Catalytic Cyclopropanation of Olefins and Diazoacetates," Bull. Chem. Soc. Jpn., vol. 68, 1995, pp. 1247-1262.

Peter Mohr et al., "249. A Study of Stereoselective Hydrolysis of Symmetrical Diesters with Pig Liver Esterase," Helevetica Chimica Acta, vol. 66, Fasc. 8, No. 249, 1983, pp. 2501-2511.

Seiichi Takano et al., "A Synthesis of Trans- and Cis-caronaldehydes," Heterocycles, vol. 23, No. 11, 1985, pp. 2859-2872.

*Primary Examiner* — Taofiq A Solola
(74) *Attorney, Agent, or Firm* — Sughrue Mion, PLLC

(57) ABSTRACT

A method of producing 6,6-dimethyl-3-oxabicyclo [3.1.0] hexan-2-one comprising subjecting a cyclopropane compound of the formula (1):

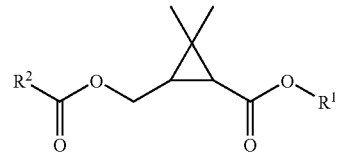

(1)

(wherein, $R^1$ represents an alkyl group, $R^2$ represents an alkyl group having carbon atom(s) of 1 to 10, a haloalkyl group having carbon atom(s) of 1 to 10, or an aryl group having carbon atoms of 6 to 10 optionally substituted by an alkyl group having carbon atom(s) of 1 to 10, and when $R^2$ represents the alkyl group, $R^1$ and $R^2$ are optionally the same or different each other.) to any of the following reactions a), b) and c):

a) an acid treatment reaction after an alkali hydrolysis reaction
b) an acid hydrolysis reaction
c) an enzyme hydrolysis reaction, then, removing an aqueous layer.

12 Claims, No Drawings

US 7,928,253 B2

METHOD OF PRODUCING 6,6-DIMETHYL-3-OXABICYCLO[3.1.0]HEXAN-2-ONE

TECHNICAL FIELD

The present invention relates to a method of producing 6,6-dimethyl-3-oxabicyclo[3.1.0]hexan-2-one.

BACKGROUND ART 6,6-dimethyl-3-oxabicyclo[3.1.0]hexan-2-one is a compound useful as various chemical product raw materials, medical and agricultural chemical intermediates and the like (see, Japanese Patent Application Laid-Open (JP-A) No. 61-183239).

As the method of producing 6,6-dimethyl-3-oxabicyclo[3.1.0]hexan-2-one, a method by a transesterification reaction of ethyl 2-acetoxymethyl -3,3-dimethylcyclopropanecarboxylate and sodium ethylate (see, JP-A No. 56-87533) and the like are mentioned.

The method of JP-A No. 56-87533, however, has a problem that separation into the intended material 6,6-dimethyl-3-oxabicyclo[3.1.0]hexan-2-one and a by-product, a trans body of 3-hydroxymethyl-2,2-dimethylcyclopropanecarboxylate is not easy, thus, this method is industrially unsatisfactory.

Under such circumstances, the present inventors have investigated a method for industrially advantageously producing 6,6-dimethyl-3-oxabicyclo[3.1.0]hexan-2-one, to find that 6,6-dimethyl-3-oxabicyclo[3.1.0]hexan-2-one can be produced efficiently by hydrolyzing 3-acyloxymethyl-2,2-dimethyl-cyclopropanecarboxylate.

DISCLOSURE OF THE INVENTION

The present invention has an object of providing a method which is capable of producing 6,6-dimethyl-3-oxabicyclo[3.1.0]hexan-2-one with good yield.

That is, the present invention provides the following [1] to [12].

[1] A method of producing 6,6-dimethyl-3-oxabicyclo[3.1.0]hexan-2-one comprising subjecting a cyclopropane compound of the formula (1):

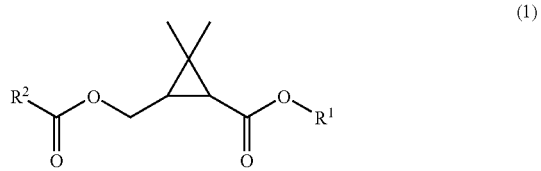

(wherein, $R^1$ represents an alkyl group, $R^2$ represents an alkyl group having carbon atom(s) of 1 to 10, a haloalkyl group having carbon atom(s) of 1 to 10, or an aryl group having carbon atoms of 6 to 10 optionally substituted by an alkyl group having carbon atom(s) of 1 to 10, and when $R^2$ represents the alkyl group, $R^1$ and $R^2$ are optionally the same or different each other.) to any of the following reactions a), b) and c):

a) an acid treatment reaction after an alkali hydrolysis reaction
b) an acid hydrolysis reaction
c) an enzyme hydrolysis reaction, then, removing an aqueous layer.

[2]. The production method according to [1], wherein the alkali hydrolysis reaction is carried out in the presence of an alkali metal hydroxide.

[3]. The production method according to [1] or [2], wherein the aqueous layer to be removed has a pH in the range of 0 to 10.

[4]. The production method according to [1] or [2], wherein the aqueous layer to be removed has a pH in the range of 6 to 8.

[5]. The production method according to any one of [1] to [4], wherein the removal of an aqueous layer is carried out in the presence of an organic solvent showing no compatibility with water.

[6]. The production method according to [5], wherein the organic solvent showing no compatibility with water is an aromatic hydrocarbon solvent.

[7]. The production method according to [6], wherein the aromatic hydrocarbon solvent is toluene.

[8]. The production method according to any one of [1] to [7], wherein the cyclopropane compound of the formula (1) is a cyclopropane compound obtained by reacting a diazoacetate of the formula (2):

$$N_2CHCO_2R^1 \qquad (2)$$

(wherein, $R^1$ represents the same meaning as described above.)

with an olefin compound of the formula (3):

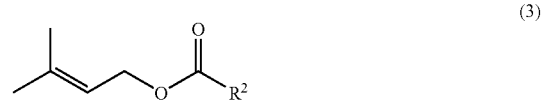

(wherein, $R^2$ represents the same meaning as described above.)

in the presence of a metal catalyst.

[9]. The production method according to [8], wherein the metal catalyst is a carboxylate of rhodium.

[10]. The production method according to [8], wherein the metal catalyst is a copper complex obtained by reacting a salicylaldimine compound of the formula 6):

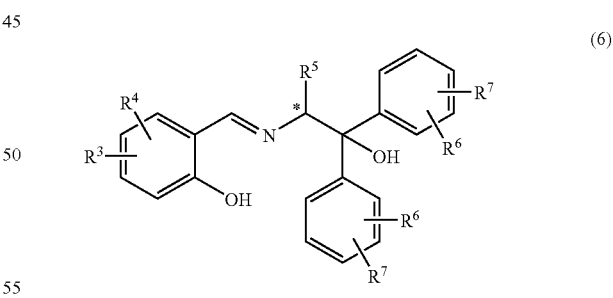

(wherein, $R^3$ and $R^4$ are optionally the same or different each other and represent a hydrogen atom, a halogen atom, a nitro group, an alkyl group having carbon atom(s) of 1 to 4, a fluoroalkyl group having carbon atom(s) of 1 to 4, an alkoxy group having carbon atom(s) of 1 to 10, an alkoxycarbonyl group having carbon atoms of 2 to 5, a trialkylsilyl group having carbon atoms of 3 to 10 or a cyano group, $R^5$ represents an alkyl group having carbon atom(s) of 1 to 4, an aryl group having carbon atoms of 6 to 10 or an aralkyl group having carbon atoms of 7 to 20, $R^6$ and $R^7$ are optionally the same or different each other and represent a hydrogen atom, an alkyl group having carbon atom(s) of 1 to 4, or an alkoxy group having carbon atom(s) of 1 to 10, and when the compound is an optically active body, * represents an asymmetrical center.)

with a copper compound.

[11]. The production method according to [10], wherein the salicylaldimine compound of the formula (6) is N-(5-nitrosalicylidene)-2-amino-1,1-di(5-tert-butyl-2-n-butoxyphenyl)-1-propanol or N-(5-nitrosalicylidene)-2-amino-1,1-di(5-tert-butyl-2-n-butoxyphenyl)-3-phenyl-1-propanol.

[12]. The production method according to [10] or [11], wherein 6,6-dimethyl-3-oxabicyclo[3.1.0]hexan-2-one in the form of optically active body is obtained with a salicylaldimine compound of the formula (6) in the form of optically active body.

EMBODIMENTS FOR CARRYING OUT THE INVENTION

The present invention will be described in detail below.

First, the cyclopropane compound of the formula (1) (hereinafter, abbreviated as cyclopropane compound (1)) will be explained.

In the formula (1), examples of the alkyl group having carbon atom(s) of 1 to 10 represented by $R^1$ or $R^2$ include linear, branched or cyclic alkyl groups such as a methyl group, ethyl group, n-propyl group, isopropyl group, n-butyl group, isobutyl group, sec-butyl group, tert-butyl group, n-hexyl group, n-octyl group, cyclohexyl group, menthyl group and the like.

Examples of the haloalkyl group having carbon atom(s) of 1 to 10 represented by $R^2$ include a chloromethyl group, trichloromethyl group and the like.

Examples of the aryl group having carbon atoms of 6 to 10 include a phenyl group, naphthyl group and the like. These aryl groups are optionally substituted by the above-described alkyl group having carbon atom(s) of 1 to 10, and examples of the aryl group substituted by the alkyl group include a 2,4,6-trimethylphenyl group and the like.

Specific examples of the cyclopropane compound (1) include methyl 3-acetoxymethyl-2,2-dimethyl-cyclopropanecarboxylate, ethyl 3-acetoxymethyl-2,2-dimethyl-cyclopropanecarboxylate, n-propyl 3-acetoxymethyl-2,2-dimethyl-cyclopropanecarboxylate, isopropyl 3-acetoxymethyl-2,2-dimethyl-cyclopropanecarboxylate, n-butyl 3-acetoxymethyl-2,2-dimethyl-cyclopropanecarboxylate, tert-butyl 3-acetoxymethyl-2,2-dimethyl-cyclopropanecarboxylate, menthyl 3-acetoxymethyl-2,2-dimethyl-cyclopropanecarboxylate, methyl 3-propionyloxymethyl-2,2-dimethyl-cyclopropanecarboxylate, ethyl 3-propionyloxymethyl-2,2-dimethyl-cyclopropanecarboxylate, n-propyl 3-propionyloxymethyl-2,2-dimethyl-cyclopropanecarboxylate, isopropyl 3-propionyloxymethyl-2,2-dimethyl-cyclopropanecarboxylate, n-butyl 3-propionyloxymethyl-2,2-dimethyl-cyclopropanecarboxylate, tert-butyl 3-propionyloxymethyl-2,2-dimethyl-cyclopropanecarboxylate, menthyl 3-propionyloxymethyl-2,2-dimethyl-cyclopropanecarboxylate, methyl 3-pivaloxymethyl-2,2-dimethyl-cyclopropanecarboxylate, ethyl 3-pivaloxymethyl-2,2-dimethyl-cyclopropanecarboxylate, n-propyl 3-pivaloxymethyl-2,2-dimethylcyclopropanecarboxylate, isopropyl 3-pivaloxymethyl-2,2-dimethyl-cyclopropanecarboxylate, n-butyl 3-pivaloxymethyl-2,2-dimethylcyclopropanecarboxylate, tent-butyl 3-pivaloxymethyl-2,2-dimethyl-cyclopropanecarboxylate, menthyl 3-pivaloxymethyl-2,2-dimethyl-cyclopropanecarboxylate, methyl 3-benzoyloxymethyl-2,2-dimethyl-cyclopropanecarboxylate, ethyl 3-benzoyloxymethyl-2,2-dimethylcyclopropanecarboxylate, n-propyl 3-benzoyloxymethyl-2,2-dimethyl-cyclopropanecarboxylate, isopropyl 3-benzoyloxymethyl-2,2-dimethyl-cyclopropanecarboxylate, n-butyl 3-benzoyloxymethyl-2,2-dimethylcyclopropanecarboxylate, tert-butyl 3-benzoyloxymethyl-2,2-dimethyl-cyclopropanecarboxylate, menthyl 3-benzoyloxymethyl-2,2-dimethyl-cyclopropanecarboxylate and the like.

The method of producing such a cyclopropane compound (1) is not particularly restricted, but includes, for example, a method of reacting a diazoacetate of the formula (2):

(wherein, $R^1$ represents the same meaning as described above.)

with an olefin compound of the formula (3):

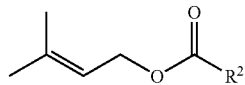

(wherein, $R^2$ represents the same meaning as described above.)

in the presence of a metal catalyst.

Examples of the diazoacetate of the above-described formula (2) (hereinafter, abbreviated as diazoacetate (2)) include methyl diazoacetate, ethyl diazoacetate, n-propyl diazoacetate, isopropyl diazoacetate, n-butyl diazoacetate, isobutyl diazoacetate, sec-butyl diazoacetate, tert-butyl diazoacetate, n-hexyl diazoacetate, n-octyl diazoacetate, cyclohexyl diazoacetate, menthyl diazoacetate and the like.

The diazoacetate (2) can be produced, for example, by reacting a corresponding aminoacetate with a diazotizing agent such as sodium nitrite and the like.

Examples of the olefin compound of the above-described formula (3) (hereinafter, abbreviated as olefin (3)) include 1-acetoxy-3-methyl-2-butene, 1-propionyloxy-3-methyl-2-butene, 1-butyryloxy-3-methyl-2-butene, 1-pivaloxy-3-methyl-2-butene, 1-chloroacetoxy-3-methyl-2-butene, 1-trichloroacetoxy-3-methyl-2-butene, 1-benzoyloxy-3-methyl-2-butene and the like.

The olefin (3) can be produced, for example, by reacting 3-methyl-2-butene-1-ol with a corresponding carboxylic halide or corresponding carboxylic anhydride in the presence of a base, however, commercially available products may also be used.

As the metal catalyst, at least one metal or compound selected from the group consisting of periodic table group VIII metals or compounds containing the metal elements; periodic table group IX metals or compounds containing the metal elements; periodic table group X metals or compounds containing the metal elements; molybdenum metal or compounds containing molybdenum element; and copper metal or compounds containing copper element (hereinafter, abbreviated as metal or compound in some cases) can be used.

The periodic table group VIII metal includes iron, ruthenium and the like, the group IX metal includes cobalt, rhodium and the like, and the group X metal includes nickel, palladium and the like.

The compounds containing the above-described metal elements include inorganic metal compounds and organic metal compounds. Examples of the inorganic metal compound include halides, carbonates, hydroxides, oxides, phosphates, sulfates, nitrates, carbon monoxide salts and the like, of the above-described metals. Examples of the organic metal compound include cyanides; carboxylates such as acetates, propionates, 2-ethylhexanoates, octanoates, stearates, trifluoroacetates, trimethylacetates, triphenylacetates, oxalates, tartarates, citrates, benzoates, N-protected amino acid salts and the like; sulfonates such as trifluoromethanesulfonate, p-toluenesulfonate and the like; acylacetonato complexes such as acetylacetonato complex, trifluoroacetylacetonato complex, hexafluoroacetylacetonato complex, benzoylacetonato complex and the like; phthalocyanine complexes such as phthalocyanine complex, hexadecafluorophthalocyanine complex, 2,3-naphthalocyanine complex and the like; cyclopentadienyl complexes such as bis(cyclopentadienyl) complex, bis(pentamethylcyclopentadienyl) complex, bis(diphenylphosphinocyclopentadienyl) complex and the like, of the above-described metals.

As the metal or compound, commercially available materials can be used, alternatively, the metal or compound may be produced by any known methods.

Complexes obtained by reacting the above-described metal or compound with a coordinative compound can also be used as the metal catalyst. Examples of such a coordinative compound include bis salicylaldimine compounds such as 1,2-diphenylethylenediamino-N,N'-bissalicylidene, 1,2-diphenylethylenediamino-N,N'-bis(5-tert-butylsalicylidene), 1,2-cyclohexanediamino-N,N'-bis(3,5-di-tert-butylsalicylidene) and the like; bisoxazoline compounds such as 2,2'-methylenebis(4-phenyl-2-oxazoline), 2,2'-methylenebis(4-isopropyl-2-oxazoline), 2,2'-methylenebis(4-tert-butyl-2-oxazoline), 2,2'-methylenebis(4-benzyl-2-oxazoline), 2,2'-methylenebis(4-phenyl-5,5-dimethyl-2-oxazoline), 2,2'-isopropylidenebis(4-phenyl-2-oxazoline), 2,2'-isopropylidenebis(4-isopropyl-2-oxazoline), 2,2'-isopropylidenebis(4-tert-butyl-2-oxazoline), 2,2'-isopropylidenebis(4-benzyl-2-oxazoline), 2,2'-isopropylidenebis(4-phenyl-5,5-dimethyl-2-oxazoline), 2,6-bis(4-isopropyl-2-oxazoline-2-yl)pyridine, 2,6-bis(4-phenyl-2-oxazoline-2-yl)pyridine and the like; amide compounds such as 4-isopropyl-2-oxazolidinone, 4-benzyl-2-oxazolidinone, 4-phenyl-2-oxazolidinone, methyl 2-pyrrolidone-5-carboxylate and the like; diamine compounds such as 1,2-diphenylethylenediamino-N,N'-bis(2,4,6-trimethylphenylmethyl) and the like; phosphine compounds such as triphenylphosphine, tricyclohexylphosphine, 2,2'-bis(diphenylphosphino)-1,1'-binaphthyl and the like; and salicylaldimine compounds described later, and the like.

For attaining the object of the present invention efficiently, it is preferable that the cyclopropane compound (1) is rich in cis body. For obtaining such a cyclopropane compound (1) rich in cis body, the above-described metal catalyst preferably includes carboxylates of rhodium such as rhodium acetate, rhodium trifluoroacetate, rhodium trimethylacetate, rhodium triphenylacetate and the like; and copper complexes obtained by reacting salicylaldimine compounds with copper compounds.

Examples of the salicylaldimine compound include salicylaldimine compounds of the formula (6) (hereinafter, abbreviated as salicylaldimine compound (6)):

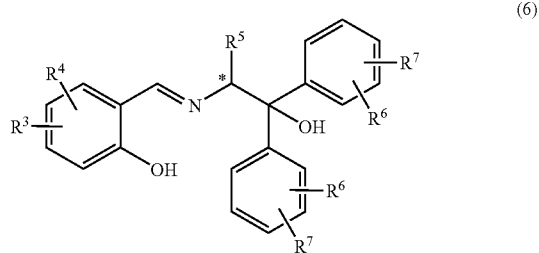

(6)

(wherein, $R^3$ and $R^4$ are optionally same or difference each other and represent a hydrogen atom, a halogen atom, a nitro group, an alkyl group having carbon atom(s) of 1 to 4, a fluoroalkyl group having carbon atom(s) of 1 to 4, an alkoxy group having carbon atom(s) of 1 to 10, an alkoxycarbonyl group having carbon atoms of 2 to 5, a trialkylsilyl group having carbon atoms of 3 to 10 or a cyano group, $R^5$ represents an alkyl group having carbon atom(s) of 1 to 4, an aryl group having carbon atom(s) of 6 to 10 or an aralkyl group having carbon atom(s) of 7 to 20, $R^6$ and $R^7$ are optionally same or difference each other and represent a hydrogen atom, an alkyl group having carbon atom(s) of 1 to 4 or an alkoxy group having carbon atom(s) of 1 to 10, and when the compound is an optically active body, * represents an asymmetrical center.).

Examples of the halogen atom represented by $R^3$ and $R^4$ include a fluorine atom, chlorine atom, bromine atom and the like.

Examples of the alkyl group having carbon atom(s) of 1 to 4 include a methyl group, ethyl group, n-propyl group, isopropyl group, n-butyl group, isobutyl group, sec-butyl group, tert-butyl group and the like.

Examples of the fluoroalkyl group having carbon atom(s) of 1 to 4 include groups in which one or more hydrogen atoms constituting an alkyl group are substituted by a fluorine atom such as a fluoromethyl group, trifluoromethyl group, fluoroethyl group, 2,2,2-trifluoroethyl group, pentafluoroethyl group, nonafluorobutyl group and the like.

Examples of the alkoxy group having carbon atom(s) of 1 to 10 include a methoxy group, ethoxy group, n-propoxy group, isopropoxy group, n-butoxy group, isobutoxy group, sec-butoxy group, tert-butoxy group, n-pentyloxy group, n-hexyloxy group, n-octyloxy group, isooctyloxy group, n-decyloxy group and the like.

Examples of the alkoxycarbonyl group having carbon atoms of 2 to 5 include a methoxycarbonyl group, ethoxycarbonyl group, n-propoxycarbonyl group, isopropoxycarbonyl group, n-butoxycarbonyl group, tert-butoxycarbonyl group and the like.

The trialkylsilyl group is a silyl group in which three hydrogens are substituted by the above-described alkyl groups which are optionally same or difference each other, and examples thereof include a trimethylsilyl group, tert-butyldimethylsilyl group and the like.

Examples of the alkyl group represented by $R^5$ include alkyl groups having carbon atom(s) of 1 to 4 such as a methyl group, ethyl group, n-propyl group, isopropyl group, n-butyl group, isobutyl group, sec-butyl group, tert-butyl group and the like. Examples of the aryl group include a phenyl group, naphthyl group and the like. Examples of the aralkyl group include a benzyl group, trityl group and the like.

Examples of the alkyl group having carbon atom(s) of 1 to 4 represented by $R^6$ and $R^7$ include a methyl group, ethyl group, n-propyl group, isopropyl group, n-butyl group, isobutyl group, sec-butyl group, tert-butyl group and the like.

Examples of the alkoxy group having carbon atom(s) of 1 to 10 include a methoxy group, ethoxy group, n-propoxy group, isopropoxy group, n-butoxy group, isobutoxy group, sec-butoxy group, tert-butoxy group, n-pentyloxy group, n-hexyloxy group, n-octyloxy group, isooctyloxy group, n-decyloxy group and the like.

Examples of such a salicylaldimine compound (6) include N-(5-nitrosalicylidene)-2-amino-1,1-di(5-tert-butyl-2-n-butoxyphenyl)-1-propanol, N-(5-nitrosalicylidene)-2-amino-1,1-di(5-tert-butyl-2-n-butoxyphenyl)-3-phenyl-1-propanol, N-(5-nitrosalicylidene)-2-amino-1,1-di(5-tert-butyl-2-n-octyloxyphenyl)-1-propanol, N-(5-nitrosalicylidene)-2-amino- 1,1-di(5-tert-butyl-2-n-octyloxyphenyl)-3-phenyl-1-propanol, N-ealicylidene-2-amino-1,1-di(5-tert-butyl-2-n-butoxyphenyl)-1-propanol, N-(5-fluorosalicylidene)-2-amino-1,1-di(5-tert-butyl-2-n-butoxyphenyl)-1-propanol, N-(5-chlorosalicylidene)-2-amino-1,1-di(5-tert-butyl-2-n-butoxyphenyl)-1-propanol, N-(5-methoxycarbonylsalicylidene)-2-amino-1,1-di(5-tert-butyl-2-n-butoxyphenyl)-1-propanol, N-(5-ethoxycarbonylsalicylidene)-2-amino-1,1-di(5-tert-butyl-2-n-butoxyphenyl)-1-propanol, N-[5-(n-propoxycarbonyl)salicylidene]-2-amino-1,1-di(5-tert-butyl-2-n-butoxyphenyl)-1-propanol, N-(5-isopropoxycarbonylsalicylidene)-2-amino-1,1-di(5-tert-butyl-2-n-butoxyphenyl)-1-propanol, N-(5-fluoromethylsalicylidene)-2-amino-1,1-di(5-tert-butyl-2-n-butoxyphenyl)-1-propanol, N-(5-difluoromethylsalicylidene)-2-amino-1,1-di(5-tert-butyl-2-n-butoxyphenyl)-1-propanol, N-(5-trifluoromethylsalicylidene)-2-amino-1,1-di(5-tert-butyl-2-n-butoxyphenyl)-1-propanol, N-salicylidene-2-amino-1,1-di(5-tert-butyl-2-n-butoxyphenyl)-3-phenyl-1-propanol, N-(5-fluorosalicylidene)-2-amino-1,1-di(5-tert-butyl-2-n-butoxyphenyl)-3-phenyl-1-propanol, N-(5-chlorosalicylidene)-2-amino-1,1-di(5-tert-butyl-2-n-butoxyphenyl)-3-phenyl-1-propanol, N-(5-methoxycarbonylsalicylidene)-2-amino-1,1-di(5-tert-butyl-2-n-butoxyphenyl)-3-phenyl-1-propanol, N-(5-ethoxycarbonylsalicylidene)-2-amino-1,1-di(5-tert-butyl-2-n-butoxyphenyl)-3-phenyl-1-propanol, N-[5-(n-propoxycarbonyl)salicylidene]-2-amino-1,1-di(5-tert-butyl-2-n-butoxyphenyl)-3-phenyl-1-propanol, N-(5-isopropoxycarbonylsalicylidene)-2-amino-1,1-di(5-tert-butyl-2-n-butoxyphenyl)-3-phenyl-1-propanol, N-(5-fluoromethylsalicylidene)-2-amino-1,1-di(5-tert-butyl-2-n-butoxyphenyl)-3-phenyl-1-propanol, N-(5-difluoromethylsalicylidene)-2-amino-1,1-di(5-tert-butyl-2-n-butoxyphenyl)-3-phenyl-1-propanol, N-(5-trifluoromethylsalicylidene)-2-amino-1,1-di(5-tert-butyl-2-n-butoxyphenyl)-3-phenyl-1-propanol, N-salicylidene-2-amino-1,1-di(5-tert-butyl-2-n-octyloxyphenyl)-1-propanol, N-(5-fluorosalicylidene)-2-amino-1,1-di(5-tert-butyl-2-n-octyloxyphenyl)-1-propanol, N-(5-chlorosalicylidene)-2-amino-1,1-di(5-tert-butyl-2-n-octyloxyphenyl)-1-propanol, N-(5-methoxycarbonylsalicylidene)-2-amino-1,1-di(5-tert-butyl-2-n-octyloxyphenyl-)-1-propanol, N-(5-ethoxycarbonylsalicylidene)-2-amino-1,1-di(5-tert-butyl-2-n-octyloxyphenyl)-1-propanol, N-[5-(n-propoxycarbonyl)salicylidene]-2-amino-1,1-di(5-tert-butyl-2-n-octyloxyphenyl)-1-propanol, N-(5-isopropoxycarbonylsalicylidene)-2-amino-1,1-di(5-tert-butyl-2-n-octyloxyphenyl)-1-propanol, N-(5-fluoromethylsalicylidene)-2-amino-1,1-di(5-tert-butyl-2-n-octyloxyphenyl)-1-propanol, N-(5-difluoromethylsalicylidene)-2-amino-1,1-di(5-tert-butyl-2-n-octyloxyphenyl)-1-propanol, N-(5-trifluoromethylsalicylidene)-2-amino-1,1-di(5-tert-butyl-2-n-octyloxyphenyl)-1-propanol, N-salicylidene2-amino-1,1-di(5-tert-butyl-2-n-octyloxyphenyl)-3-phenyl-1-propanol, N-(5-fluorosalicylidene)-2-amino-1,1-di(5-tert-butyl-2-n-octyloxyphenyl)-3-phenyl-1-propanol, N-(5-chlorosalicylidene)-2-amino-1,1-di(5-tert-butyl-2-n-octyloxyphenyl)-3-phenyl-1-propanol, N-(5-methoxycarbonylsalicylidene)-2-amino-1,1-di(5-tert-butyl-2-n-octyloxyphenyl)-3-phenyl-1-propanol, N-(5-ethoxycarbonylsalicylidene)-2-amino-1,1-di(5-tert-butyl-2-n-octyloxyphenyl)-3-phenyl-1-propanol, N-[5-(n-propoxycarbonyl)salicylidene]-2-amino-1,1-di(5-tert-butyl-2-n-octyloxyphenyl)-3-phenyl-1-propanol, N-(5-isopropoxycarbonylsalicylidene)-2-amino-1,1-di(5-tert-butyl-2-n-octyloxyphenyl)-3-phenyl-1-propanol, N-(5-fluoromethylsalicylidene)-2-amino-1,1-di(5-tert-butyl-2-n-octyloxyphenyl)-3-phenyl-1-propanol, N-(5-difluoromethylsalicylidene)-2-amino-1,1-di(5-tert-butyl-2-n-octyloxyphenyl)-3-phenyl-1-propanol, N-(5-trifluoromethylsalicylidene)-2-amino-1,1-di(5-tert-butyl-2-n-octyloxyphenyl)-3-phenyl-1-propanol, N-(6-trimethylsilylsalicylidene)-2-amino-1,1-di(5-tert-butyl-2-n-butoxyphenyl)-1-propanol, N-(6-tert-butyl-dimethylsilylsalicylidene)-2-amino-1,1-di(5-tert-butyl-2-n-butoxyphenyl)-1-propanol, N-(6-trimethylsilylsalicylidene)-2-amino-1,1-di(5-tert-butyl-2-n-butoxyphenyl)-3-phenyl-1-propanol, N-(6-tert-butyldimethylsilylsalicylidene)-2-amino-1,1-di(5-tert-butyl-2-n-butoxyphenyl)-3-phenyl-1-propanol, N-(6-trimethylsilylsalicylidene)-2-amino-1,1-di(5-tert-butyl-2-n-octyloxyphenyl)-1-propanol, N-(6-tert-butyldimethylsilylsalicylidene)-2-amino-1,1-di(5-tert-butyl-2-n-octyloxyphenyl)-1-propanol, N-(6-trimethylsilylsalicylidene)-2-amino-1,1-di(5-tert-butyl-2-n-octyloxyphenyl)-3-phenyl-1-propanol, N-(6-tert-butyldimethylsilylsalicylidene)-2-amino-1,1-di(5-tert-but1-2-n-octyloxyphenyl)-3-phenyl-1-propanol, N-(3-fluorosalicylidene)-2-amino-1,1-di(5-tert-butyl-2-n-butoxyphenyl)-3-phenyl-1-propanol, N-(3-chlorosalicylidene)-2-amino-1,1-di(5-tert-butyl-2-n-butoxyphenyl)-3-phenyl-1-propanol, N-salicylidene-2-amino-1,1-diphenyl-1-propanol, N-(3-methoxy-5-nitrosalicylidene)-2-amino-1,1-diphenyl-1-propanol, N-(3,5-dinitrosalicylidene)-2-amino-1,1-diphenyl-1-propanol, N-(5-nitrosalicylidene)-2-amino-1,1-di(2-methoxyphenyl)-1-propanol, N-(3,5-dichlorosalicylidene)-2-amino-1,1-di(2-methoxyphenyl)-1-propanol, N-(5-nitrosalicylidene)-2-amino-1,1-di(2-methoxyphenyl)-3-methyl-1-butanol, N-(3,5-di-tert-butylsalicylidene)-2-amino-1,1-di(2-methoxyphenyl)-1-propanol and the like.

As such a salicylaldimine compound (6), either racemic body or optically active body thereof may be used. When it is desired to obtain 6,6-dimethyl-3-oxabicyclo[3.1.0]hexan-2-one in the form of optically active body, a salicylaldimine compound in the form of optically active body is preferably used. The optically active salicylaldimine compound (6) includes two optical isomers, R body and S body, and any of them may be used in the present invention, and may be appropriately selected depending on desired optically active 6,6-dimethyl-3-oxabicyclo[3.1.0]hexan-2-one.

The salicylaldimine compound (6) can be produced by methods described, for example, in Tetrahedron Lett., 16, 1707 (1975), JP-A No. 2001-278853 and the like.

As the copper compound to be reacted with a salicylaldimine compound (6), monovalent or divalent copper compounds are mentioned, and examples thereof include copper carboxylates having carbon atoms of 2 to 15 such as copper (I) acetate, copper (II) acetate, copper (I) naphthenate, copper (II) naphthenate, copper (I) octylate, copper (II) octylate and the like; copper halides such as copper (I) chloride, copper (II) chloride, copper (I) bromide, copper (II) bromide and the like; copper (I) nitrate, copper (II) nitrate; copper sulfonates such as copper (I) methanesulfonate, copper (II) methanesulfonate, copper (I) trifluoromethanesulfonate, copper (II) trifluoromethanesulfonate and the like. Such copper compounds may be used each singly or in combination. These copper compounds may be in the form of anhydride or hydrate.

Preparation of a copper complex by reaction of a salicylaldimine compound (6) and a copper compound can be carried out, for example, according to methods described in JP-A No. 2001-278853, and the like.

Next, the reaction of a diazoacetate (2) and an olefin (3) in the presence of a metal catalyst (hereinafter, referred to as cyclopropanation reaction in some cases) will be described.

The use amount of an olefin (3) is usually 1 mol ratio or more based on a diazoacetate (2), and there is no particular limitation thereof, and when an olefin (3) is liquid under reaction conditions, the olefin (3) may be used in large excess amount as a solvent.

The use amount of a metal catalyst is usually 0.01 to 10 mol percent in terms of metal based on a diazoacetate (2).

The cyclopropanation reaction is usually carried out by allowing a metal catalyst, diazoacetate (2) and olefin (3) to contact and mixing them. The mixing order thereof is not particularly restricted, and for example, a diazoacetate (2) may be added to a mixture of a metal catalyst and an olefin (3), or an olefin (3) and a diazoacetate (2) may be added to a metal catalyst. An olefin (3) and a diazoacetate (2) may be added continuously or intermittently. The cyclopropanation reaction may be carried out under atmospheric pressure condition or pressure condition. The reaction temperature is usually in the range of $-20°$ C. to $150°$ C., preferably $-10°$ C. to $100°$ C.

For progressing the reaction more smoothly, a reducing agent such as for example phenylhydrazine and the like may co-exist. When a copper complex obtained by reacting a salicylaldimine compound (6) and a copper compound is used as the metal catalyst, such a reducing agent may be added in preparation of the complex. The use amount of a reducing agent is usually in the range of 0.1 to 3 mole ratio, preferably 0.9 to 1.2 mole ratio based on the metal catalyst.

This reaction is usually carried out in the presence of a solvent, and examples of the solvent include aliphatic hydrocarbon solvents such as hexane, heptane, cyclohexane and the like; aromatic hydrocarbon solvents such as toluene, xylene, monochlorobenzene, dichlorobenzene and the like; ether solvents such as tetrahydrofuran, methyl-tert-butyl ether, 1,2-dimethoxyethane, 1,4-dioxane and the like; halogenated hydrocarbon solvents such as dichloromethane, dichloroethane, chlorobutane and the like; ester solvents such as methyl acetate, ethyl acetate, butyl acetate and the like. The use amount thereof is not particularly restricted, and when economy, volume efficiency and the like are taken into consideration, it is practically 100 weight ratio or less based on a diazoacetate (2). As described above, when an olefin (3) is liquid under reaction conditions, the olefin (3) may be used as a solvent.

After completion of the reaction, if necessary, insoluble materials are removed by performing a filtration treatment, water washing treatment and the like, to obtain a mixture containing a cyclopropane compound (1). In a hydrolysis reaction of a cyclopropane compound (1), the mixture may be used as it is, alternatively, a cyclopropane compound (1) isolated by performing a usual post treatment such as distillation, column chromatography and the like may be subjected to a hydrolysis reaction.

Next, the hydrolysis reaction of a cyclopropane compound (1) will be described.

The hydrolysis reaction in the present invention is not particularly restricted providing it can hydrolyze both of two ester bonds in a cyclopropane compound (1), and may be an alkali hydrolysis reaction or an acid hydrolysis reaction. Further, it may be a hydrolysis reaction to be carried out with an enzyme or the like under neutral condition. Of them, the alkali hydrolysis reaction is preferable.

Examples of the base to be used in the alkali hydrolysis reaction include alkali metal hydroxides such as lithium hydroxide, sodium hydroxide, potassium hydroxide and the like; alkaline earth metal hydroxides such as calcium hydroxide, barium hydroxide and the like; alkali metal carbonates such as lithium carbonate, sodium carbonate, potassium carbonate and the like, and preferably, alkali metal hydroxides are used.

The use amount of the base is in the range of usually 2 to 20 mole ratio, preferably 3 to 10 mole ratio based on a cyclopropane compound (1).

Examples of the acid to be used in the acid hydrolysis reaction include inorganic acids such as hydrogen chloride, hydrogen bromide, sulfuric acid, phosphoric acid and the like; organic acids such as trifluoroacetic acid, methanesulfonic acid and the like.

The use amount of the acid is in the range of usually 2 to 20 mole ratio, preferably 3 to 10 mole ratio based on a cyclopropane compound (1).

The enzyme to be used in the enzyme hydrolysis reaction is not particularly restricted providing it has a hydrolysis ability against an ester bond in a cyclopropane compound (1), and examples thereof include ester hydrolases such as lipase, esterase and the like. These may be commercially available products, or microorganisms acting as an origin of the enzyme or treated materials thereof.

Operation of the hydrolysis reaction is carried out by stirring and mixing the above-described base, acid or enzyme with the cyclopropane compound (1) in water or a mixed solvent of water and an organic solvent.

Examples of the organic solvent include alcohol solvents such as methanol, ethanol, 2-propanol and the like; aliphatic hydrocarbon solvents such as hexane, heptane, cyclohexane and the like; aromatic hydrocarbon solvents such as toluene, xylene, monochlorobenzene, dichlorobenzene and the like; ether solvents such as tetrahydrofuran, methyl-tert-butyl ether, 1,2-dimethoxyethane, 1,4-dioxane and the like; halogenated hydrocarbon solvents such as dichloromethane, dichloroethane, chlorobutane and the like; ketone solvents such as acetone, methyl isobutyl ketone and the like; nitrile solvents such as acetonitrile, propionitrile and the like; amide solvents such as N,N'-dimethylformamide, N,N'-dimethylacetamide, N-methylpyrrolidinone and the like; ester solvents such as methyl acetate, ethyl acetate, butyl acetate and the like; and mixtures thereof, and the like.

The use amount of water is in the range of usually 0.5 to 100 weight ratio, preferably 1 to 20-weight ratio based on a cyclopropane compound (1). The use amount of the organic solvent is in the range of usually 0 to 50 weight ratio, preferably 0 to 10 weight ratio based on a cyclopropane compound (1).

The reaction temperature is in the range of usually 0 to $150°$ C., preferably 10 to $100°$ C. Progress of the reaction can be confirmed by usual analysis means such as for example gas chromatography, high performance liquid chromatography, thin layer chromatography, NMR, IR and the like.

By subjecting a reaction mixture obtained after the above-described hydrolysis reaction to a post treatment including a treatment of separation into an organic layer and an aqueous layer, 6,6-dimethyl-3-oxabicyclo[3.1.0]hexan-2-one can be selectively taken out. Such a post treatment will be described below.

The post treatment of the present invention may be a treatment in which the treatment of separation into an organic layer and an aqueous layer is performed once or more, and in addition to this, it may include usual post treatments such as a filtration treatment, extraction treatment, water washing treatment, concentration treatment and the like.

When the hydrolysis reaction is acid hydrolysis or enzyme hydrolysis, the reaction mixture is usually separated into two layers, an organic layer and an aqueous layer, and 6,6-dimethyl-3-oxabicyclo[3.1.0]hexan-2-one is present in the organic layer. When the mixture is itself separated into an organic layer and an aqueous layer, or, if necessary, mixed with water and/or an organic solvent showing no compatibility with water before separation into an organic layer and an aqueous layer, 6,6-dimethyl-3-oxabicyclo[3.1.0]hexan-2-one can be taken out as the organic layer.

When the hydrolysis reaction is an alkali hydrolysis reaction, the main product is usually present in the form of a salt of 3-hydroxymethyl-2,2-dimethylcyclopropanecarboxylic acid in an aqueous layer. When the reaction mixture after this hydrolysis reaction is treated with an acid, a cis body of 3-hydroxymethyl-2,2-dimethylcyclopropanecarboxylic acid undergoes intramolecular cyclization, to produce 6,6-dimethyl-3-oxabicyclo[3.1.0]hexan-2-one. Progress of the reaction can be confirmed by usual analysis means such as for example gas chromatography, high performance liquid chromatography, thin layer chromatography, NMR, IR and the like. Such an acid treatment includes, for example, a treatment of mixing a reaction mixture after hydrolysis with an acid and, if necessary, water, or a treatment of mixing an aqueous layer separated from a reaction mixture after hydrolysis with an acid and, if necessary, water and/or an organic solvent showing no compatibility with water, and the like. Preferable is the treatment of mixing an aqueous layer separated from a reaction mixture after hydrolysis with an acid and, if necessary, water and/or an organic solvent showing no compatibility with water.

The range of pH in the acid treatment is usually 6 or less, preferably 0 to 5. Examples of the acid to be used in the acid treatment include inorganic acids such as hydrogen chloride, hydrogen bromide, sulfuric acid, phosphoric acid and the like; and organic acids such as acetic acid, citric acid, methanesulfonic acid and the like, and preferable are inorganic acids.

A mixture obtained by an acid treatment after the alkali hydrolysis reaction is usually separated into two layers, an organic layer and an aqueous layer, and 6,6-dimethyl-3-oxabicyclo[3.1.0]hexan-2-one is present in the organic layer. When the mixture is itself separated into an organic layer and an aqueous layer, or, if necessary, mixed with water and/or an organic solvent showing no compatibility with water before separating into an organic layer and an aqueous layer, 6,6-dimethyl-3-oxabicyclo[3.1.0]hexan-2-one can be taken out as the organic layer.

In the above-described treatment of separation into an organic layer and an aqueous layer for taking out 6,6-dimethyl-3-oxabicyclo[3.1.0]hexan-2-one, when pH of the aqueous layer is too high, there is a possibility of hydrolysis of 6,6-dimethyl-3-oxabicyclo[3.1.0]hexan-2-one, while when too low, there is a possibility of inclusion of 3-hydroxymethyl-2,2-dimethylcyclopropanecarboxylic acid in large amount in the organic layer. Thus, pH of the aqueous layer in the treatment. is in the range of usually 0 to 10, preferably 6 to 8. For the pH adjustment, acids and bases can be appropriately used.

As the acid to be used for the above-described pH adjustment, those exemplified as the acid to be used for the above-described acid treatment are mentioned. Examples of the base include alkali metal hydroxides such as lithium hydroxide, sodium hydroxide, potassium hydroxide and the like; alkaline earth metal hydroxides such as calcium hydroxide, barium hydroxide and the like; alkali metal carbonates such as sodium carbonate, potassium carbonate and the like; alkaline earth metal carbonates such as calcium carbonate and the like; alkali metal bicarbonates such as sodium hydrogen carbonate, potassium hydrogen carbonate and the like; alkali metal phosphates such as disodium hydrogen phosphate, dipotassium hydrogen phosphate and the like; organic bases, such as triethylamine, pyridine and the like; ammonia, and the like, and preferably, alkali metal hydroxides.

Examples of the organic solvent showing no compatibility with water include aliphatic hydrocarbon solvents such as hexane, heptane, cyclohexane and the like; aromatic hydrocarbon solvents such as toluene, xylene, monochlorobenzene, dichlorobenzene and the like; ether solvents such as methyl-tert-butyl ether, 1,2-dimethoxyethane and the like; halogenated hydrocarbon solvents such as dichloromethane, dichloroethane, chlorobutane and the like; ketone solvents such as methyl isobutyl ketone and the like; ester solvents such as methyl acetate, ethyl acetate, butyl acetate and the like, and preferably, aromatic hydrocarbon solvents, more preferably, toluene. These solvents may be used in admixture of two or more.

The temperature of the above-described post treatment is in the range of usually 0 to 100° C., preferably, 10 to 50° C.

By performing usual isolation treatments such as concentration and the like on an organic layer containing 6,6-dimethyl-3-oxabicyclo[3.1.0]hexan-2-one obtained by the above-described post treatment, 6,6-dimethyl-3-oxabicyclo[3.1.0]hexan-2-one can be isolated.

When 3-hydroxymethyl-2,2-dimethylcyclopropanecarboxylic acid is contained as an impurity material together with 6,6-dimethyl-3-oxabicyclo[3.1.0]hexan-2-one in a treated substance after the above-described isolation treatment, 6,6-dimethyl-3-oxabicyclo[3.1.0]hexan-2-one can be purified by a distillation treatment. The distillation treatment may be carried out beyond doubt by rectification, however, purification is possible sufficiently even by simple distillation which can be carried out industrially simply. Though pressure in the distillation treatment is not particularly restricted, it is usually in the range of 0.01 to 20 KPa. The distillation temperature varies depending on the above-described pressurizing conditions, and usually in the range of 50 to 300° C.

It is also possible to conduct the above-described distillation treatment in the presence of a solvent having a higher boiling point than that of 6,6-dimethyl-3-oxabicyclo[3.1.0]hexan-2-one. By conducting a distillation operation in the presence of such a solvent, the recovery ratio of 6,6-dimethyl-3-oxabicyclo[3.1.0]hexan-2-one can be improved, giving industrial advantage. The solvent to be used for such an object is not particularly restricted providing it has higher boiling point than that of 6,6-dimethyl-3-oxabicyclo[3.1.0]hexan-2-one, and examples thereof include liquid paraffins, mineral oils, higher fatty acids, higher fatty esters and the like. Specifically, di(2-ethylhexyl) phthalate and the like are mentioned.

When a cyclopropane compound (1) in the form of raceme body is used, racemic 6,6-dimethyl-3-oxabicyclo[3.1.0]hexan-2-one is usually obtained, and when a cyclopropane compound (1) in the form of optically active body is used, optically active 6,6-dimethyl-3-oxabicyclo[3.1.0]hexan-2-one is usually obtained.

The 6,6-dimethyl-3-oxabicyclo[3.1.0]hexan-2-one thus obtained can be suitably used as chemical product raw materials such as monomers for polymer production, and the like and medical and agricultural chemical intermediates such as pyrethroid insecticides, and the like.

According to the present invention, 6,6-dimethyl-3-oxabicyclo[3.1.0]hexan-2-one can be produced with good yield, and separation from by-products can be carried out easily by performing a simple post treatment, thus, it becomes possible to provide an industrially advantageous method of producing 6,6-dimethyl-3-oxabicyclo[3.1.0]hexan-2-one.

EXAMPLES

The present invention will be illustrated in further detail based on examples below, but it is needless to say that the present invention is not limited to these examples.

Production Example 1

Synthesis of ethyl (1R, 3S)-cis-3-acetoxymethyl-2,2-dimethylcyclopropanecarboxylate The copper complex, 0.834 kg (1.20 mol), obtained by reacting copper (II) acetate and (S)-N-(5-nitrosalicylidene)-2-amino-1,1-di(5-tert-butyl-2-n-butoxyphenyl)-1-propanol, and 30.8 kg (240 mol) of 1-acetoxy-3-methyl-2-butene were dissolved in 47.2 kg of ethyl acetate and the temperature thereof was controlled to 10° C., then, 0.16 kg (1.45 mol) of phenylhydrazine was added and the mixture was stirred for 0.5 hours. Into this solution, 35.0 kg of a toluene solution containing 13.7 kg (120 mol) of ethyl diazoacetate was dropped over a period of 9 hours at the same temperature, and the mixture was thermally kept at the same temperature for 2 hours. To this solution was added 21.9 kg of an aqueous solution containing 0.5 mol of trisodium ethylenediaminetetraacetate per liter and the solution was mixed and separated, and to the resultant organic layer was further added 11.0 kg of water, mixed and separated. The solvent in the resultant organic layer was distilled off under pressure-reduced condition, then, 30.5 kg of a solution containing 19.3 kg of ethyl 3-acetoxymethyl-2,2-dimethyl-cyclopropanecarboxylate was obtained (yield based on ethyl diazoacetate: 75.0%). The cis body/trans body ratio was 83.4/16.6, and the (1R)-cis body had an optical purity of 93.4% ee.

Quantification of ethyl 3-acetoxymethyl-2,2-dimethyl-cyclopropanecarboxylate, and measurement of cis/trans ratio thereof were performed by gas chromatography. As the column, DB-WAX (0.25 μm), 0.25 mmφ×30 m manufactured by J&J was used.

On the other hand, the optical purity was measured by high performance liquid chromatography. As the column, CHIRALCEL OJ-R, 4.6 mm φ×15 cm (two) manufactured by Daicel Chemical Industries, Ltd. were used.

The boiling point of ethyl (1R, 3S)-3-acetoxymethyl-2,2-dimethyl-cyclopropanecarboxylate and results of $^1$H-NMR (CDCl$_3$ was used) are shown below.

Boiling point: 112 to 116° C. (1.0 KPa)

:δ=4.49 dd (2 H), 4.40 dd (2 H), 4.11 q (2 H), 2.05 s (3 H), 1.59 d (1 H), 1.44 dt (1 H), 1.27 s (3 H), 1.26 t (3 H), 1.20 s (3 H)

Production Example 2

Synthesis of ethyl (1S, 3R)-cis-3-acetoxymethyl-2,2-dimethylcyclopropanecarboxylate A copper complex, 30 mg (0.039 mmol), obtained by reacting copper (II) acetate and (R)-N-(5-nitrosalicylidene)-2-amino-1,1-di(5-tert-butyl-2-n-butoxyphenyl)-3-phenyl-1-propanol was dissolved in 1.2 g of ethyl acetate and a solution composed of 0.0044 mg (0.041 mmol) of phenylhydrazine and 4.5 g of ethyl acetate was added. This solution was controlled to 20° C., and a solution composed of 0.46 g (4.03 mmol) of ethyl diazoacetate and 5.15 g (40.2 mmol) of 1-acetoxy-3-methyl-2-butene was dropped over a period of 2 hours. The mixture was thermally kept at the same temperature for 0.5 hours, then, the solvent was distilled off, then, a solution containing 0.46 g of ethyl 3-acetoxymethyl-2,2-dimethylcyclopropanecarboxylate was obtained (yield based on ethyl diazoacetate: 53%). The cis body/trans body ratio was 77/23, and the (1S)-cis body had an optical purity of 86% ee.

Production Example 3

Synthesis of ethyl (1S, 3R)-cis-3-acetoxymethyl-2,2-dimethylcyclopropanecarboxylate A solution containing 0.59 g of ethyl 3-acetoxymethyl-2,2-dimethylcyclopropanecarboxylate was obtained (yield based on ethyl diazoacetate: 68%) in the same manner as in Example 2 excepting that 27 mg (0.039 mmol) of a copper complex obtained by reacting copper (II) acetate and (R)-N-(5-nitrosalicylidene)-2-amino-1,1-di(5-tert-butyl-2-n-butoxyphenyl)-1-propanol was used instead of the copper complex in Production Example 2. The'cis body/trans body ratio was 75/25, and the (1S)-cis body had an optical purity of 91% ee.

Production Example 4

Synthesis of racemic ethyl cis-3-acetoxymethyl-2,2-dimethylcyclopropanecarboxylate Rhodium triphenylacetate, 6.78 mg (0.01 mmol), was dissolved in 9.0 g of ethyl acetate, and 2.56 g (20.0 mmol) of 1-acetoxy-3-methyl-2-butene was added, then, the temperature thereof was raised to 50° C. Into this solution, a solution composed of 1.14 g (10.0 mmol) of ethyl diazoacetate and 3.6 g of ethyl acetate was dropped over a period of 2 hours, and the mixture was, thermally kept at the same temperature for 0.5 hours. To this solution was added an aqueous solution containing 0.5 mol of trisodium ethylenediaminetetraacetate per liter and the solution was mixed and separated, and a solution containing 1.82 g of ethyl 3-acetoxymethyl-2,2-dimethylcyclopropanecarboxylate was obtained (yield based on ethyl diazoacetate: 84.8%). The cis body/trans body ratio was 72/28.

Production Example 5

Synthesis of ethyl (1R, 3S)-cis-3-acetoxymethyl-2,2-dimethylcyclopropanecarboxylate 278 mg (0.40 mmol) of a copper complex obtained by reacting copper (II) acetate and (S)-N-(5-nitrosalicylidene)-2-amino-1,1-di(5-tert-butyl-2-n-butoxyphenyl)-1-propanol was dissolved in 15.75 g (122.9 mmol) of 1-acetoxy-3-methyl-2-butene. This solution was controlled to 10° C., and a solution composed of 0.053 g (0.48 mmol) of phenyl-hydrazine and 0.46 g (3.6 mmol) of 1-acetoxy-3-methyl-2-butene was added, and the mixture was thermally kept at the same temperature for 5 minutes, then, a solution composed of 4.56 g (40.0 mmol) of ethyl diazoacetate, 5.33 g (41.6 mmol) of 1-acetoxy-3-methyl-2-butene and 3.60 g of toluene was dropped over a period of 10 hours. The mixture was thermally kept at the same temperature for 0.5 hours, then, to this solution was added 8.0 g of an aqueous solution containing 0.5 mol of trisodium ethylenediaminetetraacetate per liter and the solution was mixed and separated, and 33.23 g of a solution containing 6.81 g of ethyl 3-acetoxymethyl-2,2-dimethyl-cyclopropanecarboxylate was obtained (yield based on ethyl diazoacetate: 79.5%). The cis body/trans body ratio was 83.1/16.9, and the (1R)-cis body had an optical purity of 90.8% ee.

Example 1

Synthesis of (1R, 5S)-6,6-dimethyl-3-oxabicyclo [3.1.0] hexan-2-one

To 13.5 kg of a solution containing 8.53 kg of ethyl 3-acetoxymethyl-2,2-dimethylcyclopropanecarboxylate obtained in Production Example (39.8 mol, cis body/trans body ratio was 83.4/16.6, (1R)-cis body had an optical purity of 93.4% ee), 9.1 kg of water was added and the temperature thereof was raised up to 50° C., then, 24.2 kg of a 28% sodium hydroxide aqueous solution was dropped over a period of 4 hours, and the mixture was thermally kept at the same temperature for 2 hours. It was confirmed that ethyl 3-acetoxymethyl-2,2-dimethylcyclopropanecarboxylate disappeared and was converted into 3-hydroxymethyl-2,2-dimethylcyclopropanecarboxylic acid, then, to this solution was added 25.6 kg of toluene and the solution was mixed and separated, and the organic layer was removed. Further, to the aqueous layer was added 17.1 kg of toluene and the solution was mixed and separated, and the organic layer was removed likewise. To the resultant aqueous layer was added 21.8 kg of 35% hydrochloric acid at 20° C. and the mixture was thermally kept for 3 hours. It was confirmed that cis-3-hydroxymethyl-2,2-dimethyl-cyclopropanecarboxylic acid was converted into 6,6-dimethyl-3-oxabicyclo[3.1.0]hexan-2-one, then, a 28% sodium hydroxide aqueous solution was dropped to adjust pH of the solution to 7. An extraction operation was repeated three times from this solution with 17.1 kg of toluene, and the resultant three toluene solutions were combined, to obtain 55.7 kg of a toluene solution containing 4.05 kg of 6,6-dimethyl-3-oxabicyclo[3.1.0]hexan-2-one (32.1 mol, yield based on ethyl cis-3-acetoxymethyl-2,2-dimethylcyclopropanecarboxylate: 96.7%). In this toluene solution, trans-3-hydroxymethyl-2,2-dimethylcyclopropanecarboxylic acid was not detected.

Example 2

Synthesis of (1R, 5S)-6,6-dimethyl-3-oxabicyclo[3.1.0]hexan-2-one

A solution (747 g) containing 512.1 g of ethyl 3-acetoxymethyl-2,2-dimethylcyclopropanecarboxylate (2.39 mol, cis body/trans body ratio was 80.3/19.7, (1R)-cis body had an optical purity of 93.3% ee) was heated up to 50° C., then, 1975 g of a 20% sodium hydroxide aqueous solution was dropped, and the mixture was thermally kept at the same temperature for 10 hours. To this solution was added 1536 g of toluene and the solution was mixed and separated, and the organic layer was removed.

Further, to the aqueous layer was added 1024 g of toluene and the solution was mixed and separated, and the organic layer was removed. To the resultant aqueous layer was added 1277 g of 35% hydrochloric acid and the mixture was thermally kept at 50° C. for 1 hour.

From 4041 g of the resultant solution, 20.1 g of that was used, and the subsequent cis body/trans body separation operation was carried out. Into 20.1 g of this solution, a 20% sodium hydroxide aqueous solution was dropped, to adjust pH of the solution to 3. An extraction operation was repeated three times from this solution with 7.8 kg of toluene, and the resultant organic layers were combined. Then, toluene was distilled off, then, 1.49 g of a solution containing 1.17 g of 6,6-dimethyl-3-oxabicyclo[3.1.0]hexan-2-one (9.27 mmol, yield based on ethyl cis-3-acetoxymethyl-2,2-dimethylcyclopropanecarboxylate: 97.2%, (1R, 5S)-body had an optical purity of 92.8% ee) was obtained. In this toluene solution, 0.057 g (0.39 mmol) of trans-3-hydroxymethyl-2, 2-dimethylcyclopropanecarboxylic acid was present.

This solution could be further distilled at 150° C. and under a reduced pressure of 1.3 kPa to completely separate and purify trans-3-hydroxymethyl-2,2-dimethylcyclopropanecarboxylic acid and 6,6-dimethyl-3-oxabicyclo[3.1.0]hexan-2-one.

Example 3

Synthesis of (1R, 5S)-6,6-dimethyl-3-oxabicyclo[3.1.0]hexan-2-one 1.46 g of a solution containing 1.20 g of 6,6-dimethyl-3-oxabicyclo[3.1.0]hexan-2-one (9.49 mmol, yield based on ethyl cis-3-acetoxymethyl-2,2-dimethylcyclopropanecarboxylate: 99.4%, (1R, 5S)-body had an optical purity of 92.8% ee) was obtained in the same manner as in Example 7 excepting that pH was 1 in extracting 6,6-dimethyl-3-oxabicyclo[3.1.0]hexan-2-one with toluene in Example 2. In this toluene solution, 0.062 g (0.43 mmol) of trans-3-hydroxymethyl-2,2-dimethylcyclopropanecarboxylic acid was present.

This solution could be further distilled at 150° C. and under a reduced pressure of 1.3 kPa to separate trans-3-hydroxymethyl-2,2-dimethylcyclopropanecarboxylic acid and 6,6-dimethyl-3-oxabicyclo[3.1.0]hexan-2-one.

The invention claimed is:

1. A method of producing 6,6-dimethyl-3-oxabicyclo[3.1.0]hexan-2-one comprising subjecting a cyclopropane compound of the formula (1):

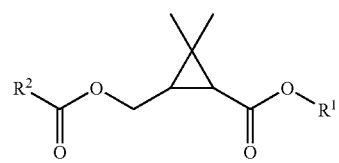

(1)

wherein, $R^1$ represents an alkyl group, $R^2$ represents an alkyl group having carbon atom(s) of 1 to 10, a haloalkyl group having carbon atom(s) of 1 to 10, or an aryl group having carbon atoms of 6 to 10 optionally substituted by an alkyl group having carbon atom(s) of 1 to 10, and when $R^2$ represents the alkyl group, $R^1$ and $R^2$ are optionally the same or different each other to any of the following reactions a), b) and c):
a) an acid treatment reaction after an alkali hydrolysis reaction;
b) an acid hydrolysis reaction; or
c) an enzyme hydrolysis reaction
then, removing an aqueous layer.

2. The production method according to claim 1, wherein the alkali hydrolysis reaction is carried out in the presence of an alkali metal hydroxide.

3. The production method according to claim 1, wherein the aqueous layer to be removed has a pH in the range of 0 to 10.

4. The production method according to claim 1, wherein the aqueous layer to be removed has a pH in the range of 6 to 8.

5. The production method according to claim 1, wherein the removal of an aqueous layer is carried out in the presence of an organic solvent showing no compatibility with water.

6. The production method according to claim 5, wherein the organic solvent showing no compatibility with water is an aromatic hydrocarbon solvent.

7. The production method according to claim 6, wherein the aromatic hydrocarbon solvent is toluene.

8. The production method according to claim 1, wherein the cyclopropane compound of the formula (1) is a cyclopropane compound obtained by reacting a diazoacetate of the formula (2):

$$N_2CHCO_2R^1 \quad (2)$$

wherein, $R^1$ represents the same meaning as described above with an olefin compound of the formula (3):

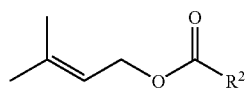
(3)

wherein, $R^2$ represents the same meaning as described above in the presence of a metal catalyst.

9. The production method according to claim 8, wherein the metal catalyst is a carboxylate of rhodium.

10. The production method according to claim 8, wherein the metal catalyst is a copper complex obtained by reacting a salicylaldimine compound of the formula (6):

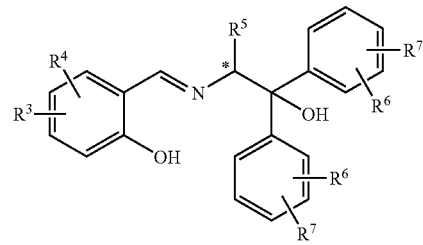
(6)

wherein, $R^3$ and $R^4$ are optionally the same or different each other and represent a hydrogen atom, a halogen atom, a nitro group, an alkyl group having carbon atom(s) of 1 to 4, a fluoroalkyl group having carbon atom(s) of 1 to 4, an alkoxy group having carbon atom(s) of 1 to 10, an alkoxycarbonyl group having carbon atoms of 2 to 5, a trialkylsilyl group having carbon atoms of 3 to 10 or a cyano group, $R^5$ represents an alkyl group having carbon atom(s) of 1 to 4, an aryl group having carbon atoms of 6 to 10 or an aralkyl group having carbon atoms of 7 to 20, $R^6$ and $R^7$ are optionally the same or different from each other and represent a hydrogen atom, an alkyl group having carbon atom(s) of 1 to 4, or an alkoxy group having carbon atom(s) of 1 to 10, and when the compound is an optically active body, * represents an asymmetrical center with a copper compound.

11. The production method according to claim 10, wherein the salicylaldimine compound of the formula (6) is N-(5-nitrosalicylidene)-2-amino-1,1-di(5-tert-butyl-2-n-butoxyphenyl)-1-propanol or N-(5-nitrosalicylidene)-2-amino-1,1-di(5-tert-butyl-2-n-butoxyphenyl)-3-phenyl-1-propanol.

12. The production method according to claim 10, wherein 6,6-dimethyl-3-oxabicyclo[3.1.0]hexan-2-one in the form of optically active body is obtained with a salicylaldimine compound of the formula (6) in the form of optically active body.

* * * * *